United States Patent
Simpson et al.

(10) Patent No.: US 9,451,999 B2
(45) Date of Patent: Sep. 27, 2016

(54) SURGICAL INSTRUMENT ADAPTOR

(71) Applicant: Warsaw Orthopedic, Inc., Warsaw, IN (US)

(72) Inventors: Joshua W. Simpson, Collieville, TN (US); William A. Rezach, Atoka, TN (US); Nicholas M. Benson, Cordova, TN (US); Grant D. Foy, Memphis, TN (US); Thomas V. McGahann, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 373 days.

(21) Appl. No.: 14/050,855

(22) Filed: Oct. 10, 2013

(65) Prior Publication Data

US 2015/0105833 A1    Apr. 16, 2015

(51) Int. Cl.
| | |
|---|---|
| *A61B 17/88* | (2006.01) |
| *A61B 17/70* | (2006.01) |
| *A61B 5/06* | (2006.01) |
| *A61B 17/16* | (2006.01) |
| *A61B 17/90* | (2006.01) |
| *A61B 17/00* | (2006.01) |

(52) U.S. Cl.
CPC .............. *A61B 17/7082* (2013.01); *A61B 5/06* (2013.01); *A61B 17/162* (2013.01); *A61B 17/7076* (2013.01); *A61B 17/8875* (2013.01); *A61B 2017/00477* (2013.01); *A61B 2017/90* (2013.01); *A61B 2034/2055* (2016.02); *A61B 2090/3966* (2016.02); *A61B 2090/3983* (2016.02)

(58) Field of Classification Search
CPC .......... A61B 5/06; A61B 2017/00477; A61B 17/7076; A61B 17/7082; A61B 17/8875; A61B 2017/90; A61B 19/5244; A61B 2019/5466
See application file for complete search history.

(56) References Cited

U.S. PATENT DOCUMENTS

| | | | | |
|---|---|---|---|---|
| 6,021,343 | A  * | 2/2000  | Foley      | A61B 17/16 600/417 |
| 6,840,143 | B1 * | 1/2005  | Lin        | B25B 23/0035 81/177.85 |
| 2004/0231468 | A1 * | 11/2004 | Odachowski | B25B 15/02 81/58.1 |
| 2010/0107828 | A1 * | 5/2010  | Huerta     | B25B 13/461 81/177.9 |
| 2012/0253323 | A1 * | 10/2012 | Bharadwaj  | A61B 17/8883 606/1 |
| 2013/0004916 | A1 * | 1/2013  | Bellanca   | A61C 8/0018 433/173 |
| 2013/0261609 | A1 * | 10/2013 | Dicorleto  | A61B 17/1622 606/1 |

* cited by examiner

*Primary Examiner* — Larry E Waggle, Jr.

(57) ABSTRACT

A surgical instrument adaptor comprises a member that defines a longitudinal axis. The member is configured for connection to an image guide that is configured to generate a signal representative of a position of a surgical instrument. The member extends between a first end and a second end. The first end includes a first mating part configured for releasable engagement with a mating part of an actuator. The second end includes a second mating part configured for releasable engagement with a mating part of the surgical instrument. Systems and methods are described.

19 Claims, 6 Drawing Sheets

SURGICAL INSTRUMENT ADAPTOR

TECHNICAL FIELD

The present disclosure generally relates to medical devices for the treatment of musculoskeletal disorders, and more particularly to an instrument of a surgical system employed for performing a surgical procedure and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, implants such as bone fasteners, connectors, plates and vertebral rods are often used to provide stability to a treated region. These implants can redirect stresses away from a damaged or defective region while healing takes place to restore proper alignment and generally support the vertebral members. Surgical instruments, such as wires and cannulated instrumentation, can be employed to establish passageways for delivery of the implants and/or fasten the implants with the vertebral members. This disclosure describes an improvement over these prior art technologies.

SUMMARY

In one embodiment, a surgical instrument adaptor is provided. The adaptor comprises a member that defines a longitudinal axis. The member is configured for connection to an image guide that is configured to generate a signal representative of a position of a surgical instrument. The member extends between a first end and a second end. The first end includes a first mating part configured for releasable engagement with a mating part of an actuator. The second end includes a second mating part configured for releasable engagement with a mating part of the surgical instrument. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system are discussed in terms of medical devices for the treatment of musculoskeletal disorders and more particularly, in terms of a surgical implant system for delivering and/or fastening implants with a surgical site and a method for treating a spine.

In one embodiment, the system includes a surgical instrument adaptor that has an adaptable and changeable configuration that can be used with the working ends of alternate surgical instruments. In one embodiment, this configuration aids in the transfer of the surgical instrument from the table to the surgeon. In one embodiment, the surgical instrument adaptor is connected with a navigational component and an actuator, which is also connected with a driver. This configuration allows for alternate drivers to be connected with the actuator via the surgical instrument adaptor.

In one embodiment, the surgical instrument adaptor includes a bushing for engagement with a navigational component. In one embodiment, the surgical instrument adaptor includes a square connection end for engagement with an actuator. In one embodiment, the surgical instrument adaptor includes an elongated shaft that slides into a surgical instrument to prevent toggle. In one embodiment, the surgical instrument adaptor engages a driver with a friction fit to allow for a substantially rigid connection between the driver and the adaptor. In one embodiment, a driving feature includes a load bearing portion. In one embodiment, the connection between the adaptor and the driver includes a keyed joint configuration, for example, in those applications requiring directional control.

In one embodiment, a single driver is provided that is connected to the surgical instrument adaptor, which is connected to the navigation component and the motorized and/or manual actuator such that the adaptor is utilized for connection to alternate instruments. In one embodiment, a set, system and/or kit of adapters can be used with different instrumentation. In some embodiments, the surgical instrument adaptor is employed with a navigation, manual or powered system. In one embodiment, the surgical instrument adaptor connects an instrument and a driving device so that a single instrument can be used with an adaptor with different drivers.

In some embodiments, one or all of the components of the system may be disposable, peel pack and/or pre packed sterile devices. One or all of the components of the system may be reusable. The system may be configured as a kit with multiple sized and configured components.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or anterolateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including surgical instruments, related components and methods of employing the surgical system. Alternate embodiments are also disclosed. Reference is made in detail to the exemplary embodiments of the present disclosure, which are illustrated in the accompanying figures. Turning to FIGS. 1-6, there are illustrated components of a spinal implant system 10, in accordance with the principles of the present disclosure.

The components of spinal implant system 10 can be fabricated from biologically acceptable materials suitable for medical applications, including metals, synthetic polymers, ceramics and bone material and/or their composites, depending on the particular application and/or preference of a medical practitioner. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with an open or mini-open, minimal access and/or minimally invasive including percutaneous surgical technique to create a cavity for an implant, such as, for example, a bone fastener at a surgical site within a body of a patient, for example, a section of a spine. In one embodiment, the components of spinal implant system 10 are configured to create a cavity in vertebrae to fix a spinal rod, connector and/or plate to a spine via a bone fastener for a surgical treatment to treat various spine pathologies, such as those described herein.

Figure 1:
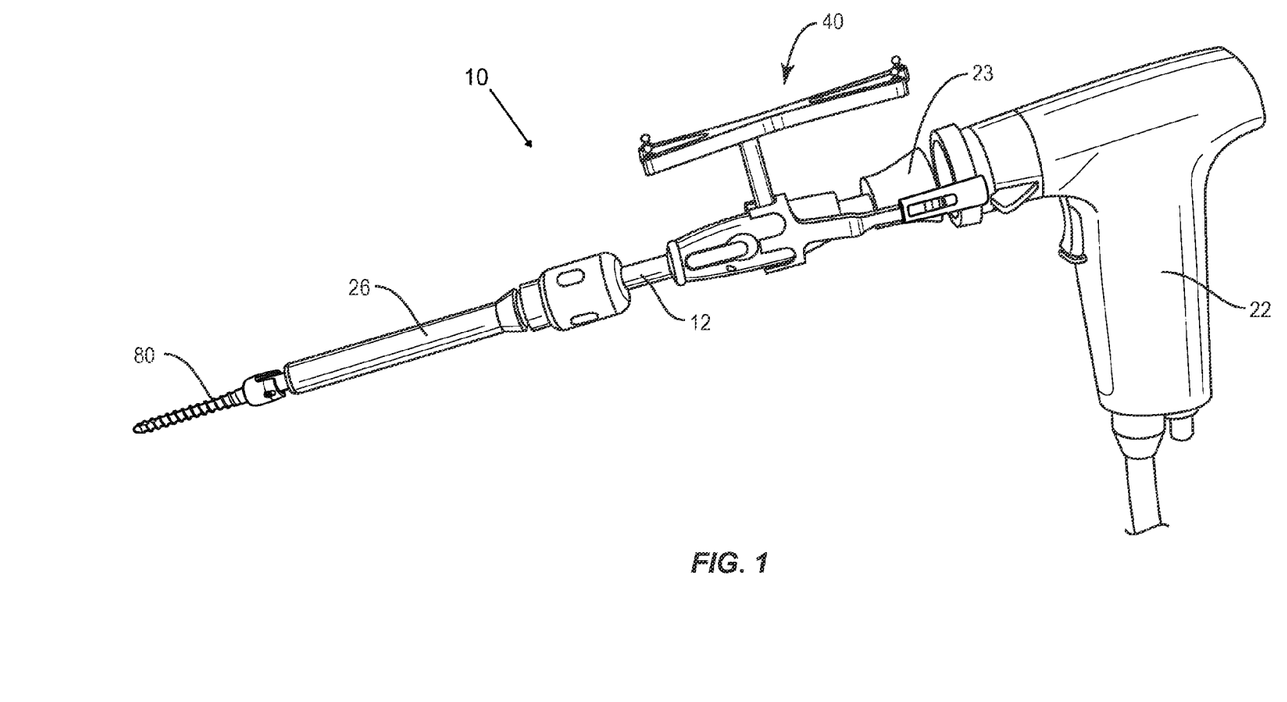
FIG. 1 is a perspective view of components of one embodiment of a surgical system in accordance with the principles of the present disclosure.
Figure 2:
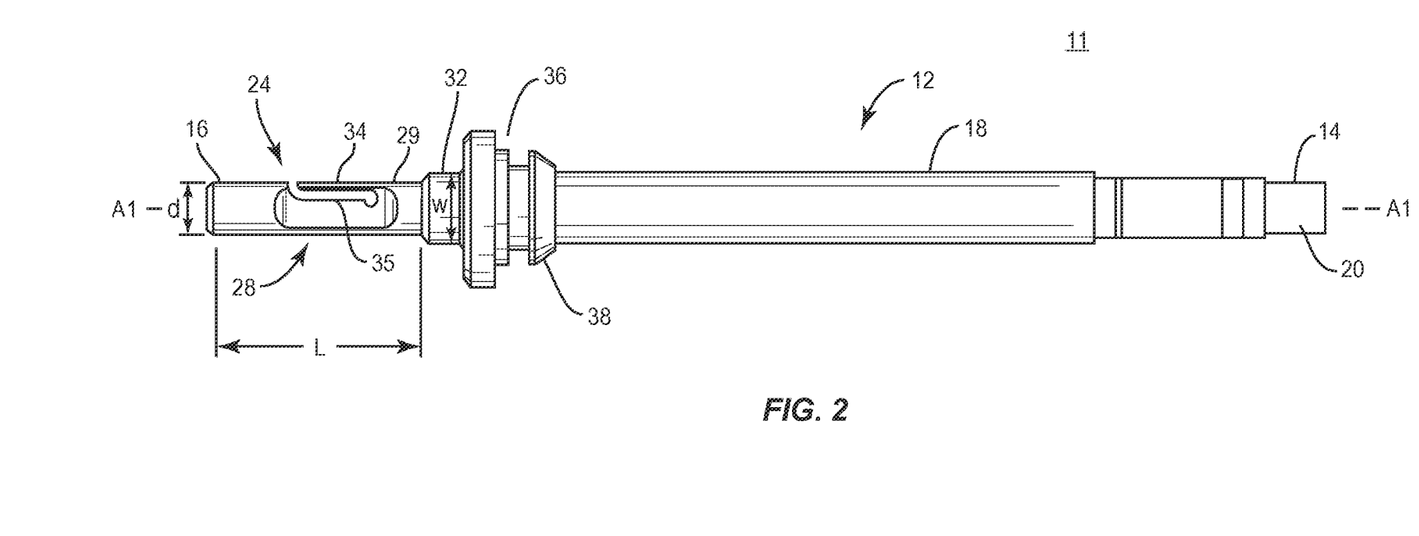
FIG. 2 is a side view of a component of the system shown in FIG. 1.

Spinal implant system 10 includes an adaptor 11, as shown in FIG. 2. Adaptor 11 includes a member, such as, for example, a shaft 12. Shaft 12 defines a longitudinal axis A1 and extends between an end 14 and an end 16. End 14 is configured for connection to a surgical instrument, as discussed herein. End 14 is configured for connection to an actuator, as discussed herein. Shaft 12 includes an outer surface 18 configured for connection with an image guide, as discussed herein.

Figure 5:
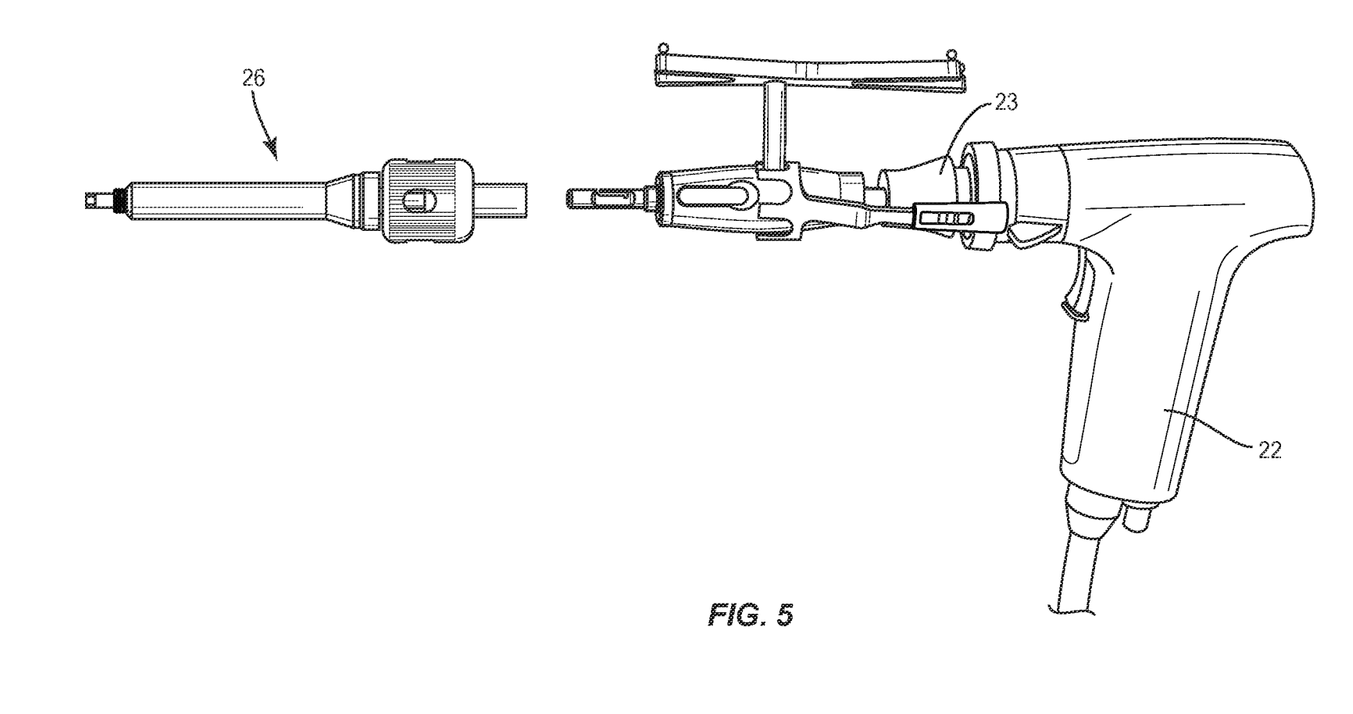
FIG. 5 is a side view of components of the system shown in FIG. 1 with parts separated.

End 14 defines a connection portion 20 configured for releasable engagement with an actuator 22, such as, for example, a powered drill, hand drill or other tool, as shown in FIG. 5. In one embodiment, connection portion 20 includes a male mating portion and actuator 22 includes a corresponding female mating portion (not shown). The female mating portion 22 of adaptor 22 may include a chuck, collet or other mating structure. In one embodiment, connection portion 20 has a square cross sectional configuration and is configured to engage a correspondingly shaped portion of a mating portion 23 of actuator 22. In some embodiments, connection portion 20 may include a hexagonal, triangular, polygonal, star or hexalobe cross sectional configuration configured engage a correspondingly shaped portion of mating portion 23. Actuator 22 is configured to rotate a surgical tool, in the direction shown by arrow B and/or the direction shown by arrow BB in FIG. 6. Connection portion 20 is configured to mate with alternate actuators.

Figure 4:
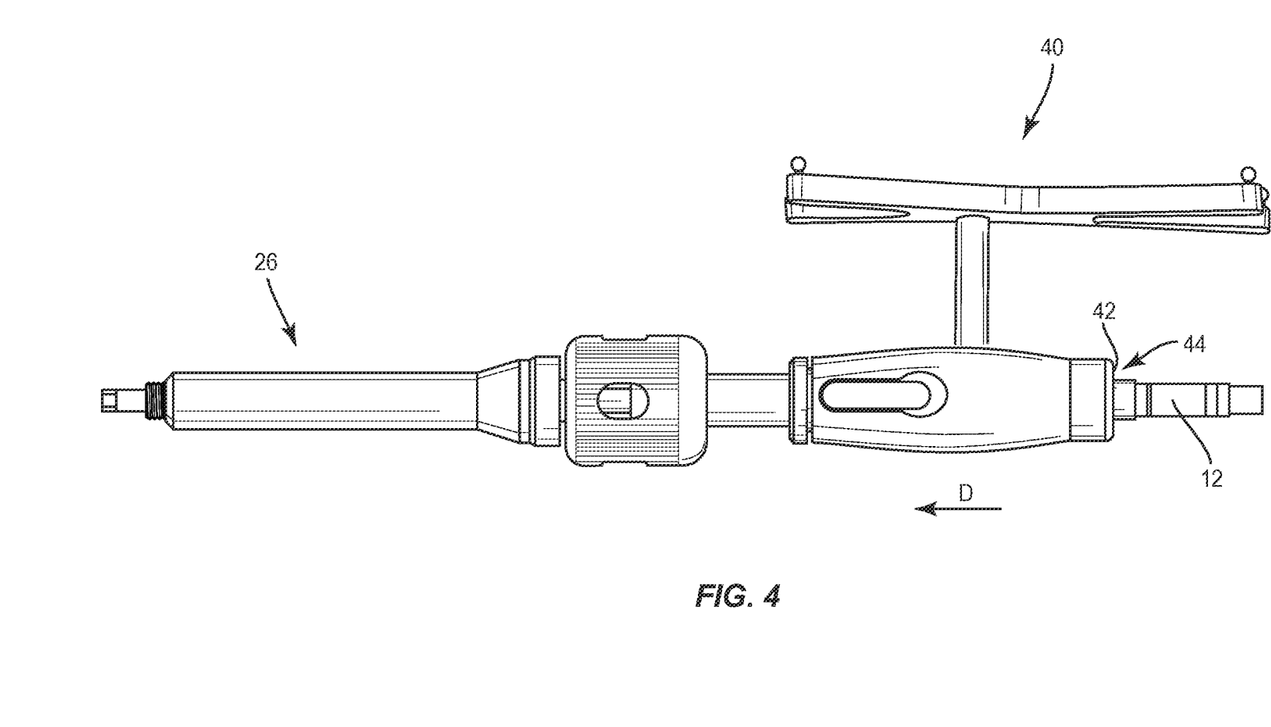
FIG. 4 is a side view of components of the system shown in FIG. 1.

End 16 includes a connection portion 24 configured for releasable engagement with a surgical tool, such as, for example, a driver 26, as shown in FIG. 4. Connection portion 24 includes an elongated section 28 and an outer surface 29 configured for engagement with an inner surface 31 that defines a cavity 30 of driver 26. In one embodiment, connection portion 24 includes a male mating portion and driver 26 includes a corresponding female mating portion (not shown). Section 28 includes a length L and a diameter d. In one embodiment, length L is larger than diameter d, such as, for example, length L is five times longer than diameter d. This configuration prevents axial toggle of connection portion 24 with driver 26.

Connection portion 24 includes an interference fit, such as, for example, a friction fit connection between surface 29 and inner surface 31 of cavity 30 of driver 26. In one embodiment, section 28 has diameter d that creates a friction fit with surface 31 of cavity 30. In one embodiment, cavity 30 includes a diameter d2 that is nominally smaller than diameter d and forms the friction fit when connected. Section 28 is disposed in cavity 30 of driver 26 such that surface 31 and surface 18 engage in a friction or interference fit to resist and/or prevent rotation of surface 18 of shaft 12 relative to surface 31 of driver 26. Section 28 and driver 26 fit together creating a frictional engagement between section 28 and surface 31. In some embodiments, all or only a portion of surface 19 and/or surface 31 may have alternate surface configurations to enhance engagement with one another such as, for example, rough, arcuate, undulating, mesh, porous, semi-porous, dimpled and/or textured, according to the requirements of a particular application. Connection portion 24 is configured to mate with alternate surgical tools as required for a particular surgical procedure.

In one embodiment, connection portion 24 is connected with driver 26 via a keyed joint connection. In one embodiment, section 28 includes a resilient flange 34 configured to mate with a corresponding shaped portion in cavity 30 (not shown), such as, for example, a keyseat. In one embodiment, flange 34 is monolithically formed with section 28 and includes an inner surface 35 having an arcuate configuration for releasable engagement with a corresponding shaped portion of cavity 30. In one embodiment, flange 34 can be integrally connected with section 28 or include fastening elements. Engagement of section 28 with cavity 30 requires alignment of flange 34 with a corresponding opening in cavity 30. As flange 34 is inserted into cavity 30, flange 34 engages a corresponding shaped portion within cavity 30. In one embodiment, flange 34 is depressed such that flange 34 moves towards surface 35 as it translates through cavity 30. The biasing force of flange 34 to move away from surface 35 allows flange 34 to deflect and lock with cavity 30. In some embodiments, other keyway configurations are contemplated, such as, for example, oval, oblong, triangular, square, hexagonal, polygonal, irregular, uniform, nonuniform and/or tapered. The keyed joint prevents relative rotation between section 28 and driver 26 and enables torque transmission. The keyed joint configuration is used for temporary fastening and allows for relative axial movement between section 28 and driver 26. This keyed joint configuration allows for directional control over the connection between shaft 12 and driver 26.

Figure 3:
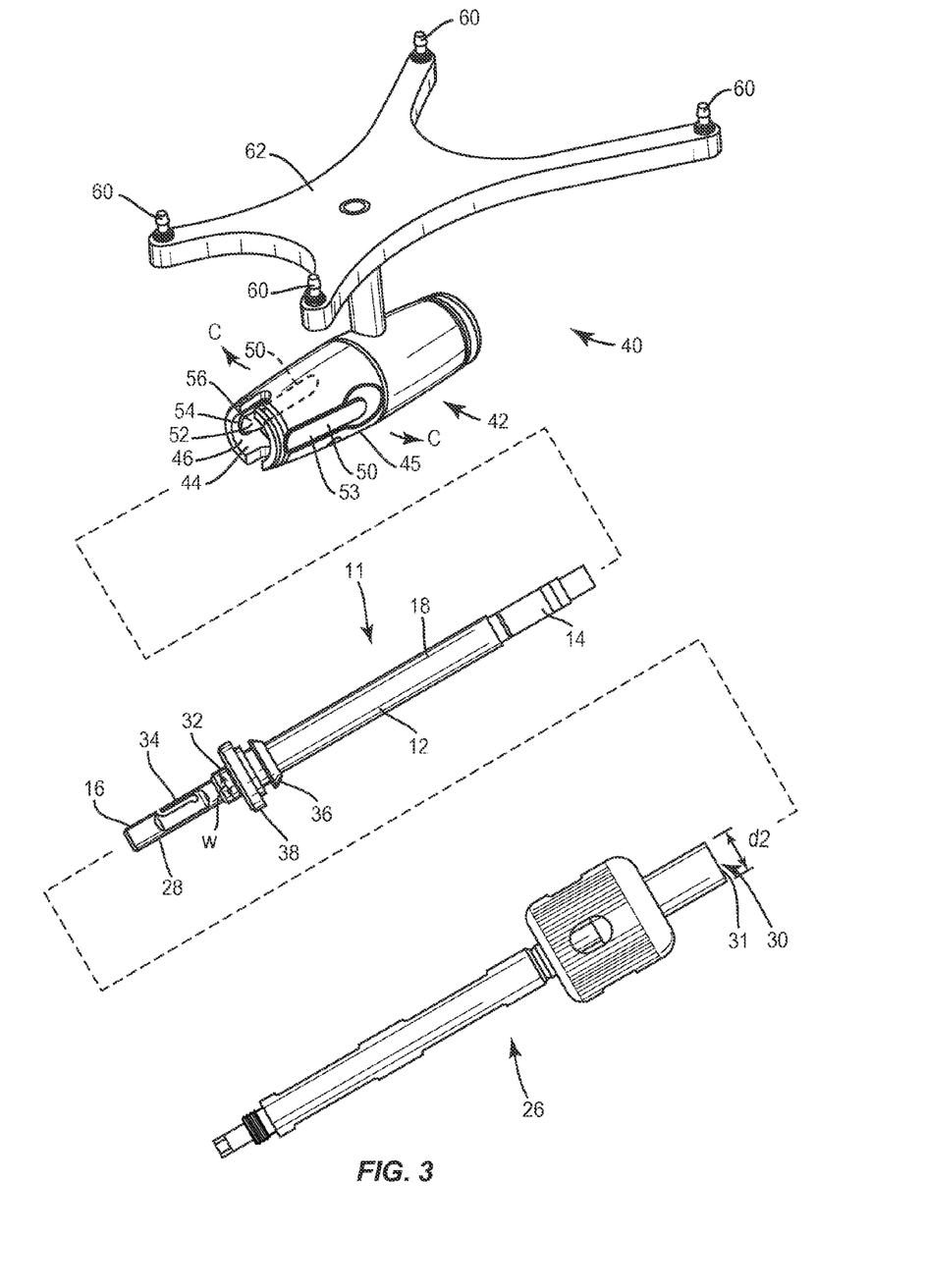
FIG. 3 is a perspective view of components of the system shown in FIG. 1 with parts separated.

In one embodiment, section 28 includes a torque engagement portion 32 configured to facilitate transmission of torque from actuator 22 to driver 26. As shown in FIG. 3, portion 32 includes a hexagonal cross section having a width w equal to diameter d2 such that a close fitting engagement and/or interference fit is created between portion 32 and cavity 30. Cavity 30 of driver 26 includes a hexagonal cross section configured to mate with portion 32. As driver 26 translates over section 28, cavity 30 mates with portion 32. In some embodiments, portion 32 may have alternate cross section configurations, such as, for example, oval, oblong, triangular, square, polygonal, irregular, uniform, non-uniform and/or tapered.

Spinal implant system 10 includes an image guide, such as, for example, an navigation component 40, as shown in FIG. 3, configured to generate a signal representative of a position of driver 26. Navigation component 40 is configured for disposal with surface 18 of shaft 12. A connection mechanism, such as, for example, a circumferential flange 36 is disposed with surface 18 of shaft 12 at a position between end 14 and end 16. In some embodiments, flange 36 can be disposed at other various positions along shaft 12. In one embodiment, navigation component 40 includes a collar 42 having an inner surface 44 and an outer surface 45. Surface 44 defines a passageway 46. Surface 44 is configured for releasable engagement with flange 36. Passageway 46 is configured to receive shaft 12. Surface 44 defines at least one resilient tab 50. In one embodiment, collar 42 includes a plurality of tabs 50, as shown in FIG. 3. Each tab 50 includes an inner surface 52 that defines a cutout 54 and an outer surface 53. Each cutout 54 includes raised portions 56 that define edges of cutout 54. Cutout 54 is configured to receive flange 36. In its initial position, surface 53 is aligned with surface 45 of collar 42.

Translation of collar 42 over shaft 14, in the direction shown by arrow D in FIG. 4, causes flange 36 to engage portions 56 such that flange 36 applies a force to tabs 50 to move tabs 50 outwardly, in the direction shown by arrows C in FIG. 3, such that surface 53 is deflected from surface 45. As flange 36 translates over portion 56, flange 36 moves into cutouts 54 allowing tabs 50 to move back to their initial position. In some embodiments, guide 40 is configured for removable engagement with shaft 12, as shown in FIG. 3. In some embodiments, navigation component 40 may be integrally formed with shaft 12 such that shaft 12 is a monolithic, unitary body. In one embodiment, surface 18 includes a bushing 38 configured to engage collar 42 of navigation component 40 to reduce vibrations resulting from the torque of the actuator.

In some embodiments, navigation component 40 may include one or a plurality of guides. In one embodiment, navigation component 40 is shaped substantially like the Greek letter pi and comprises four spaced apart arms including emitters 60 for generating a signal representing the trajectory of driver 26 relative to a portion of a patient's anatomy and the depth of a screw within the patient's anatomy. In one embodiment, navigation component 40 includes at least one light emitting diode. In some embodiments, navigation component 40 may include other tracking devices capable of being tracked by a corresponding sensor array, such as, for example, a tracking device that actively generates acoustic signals, magnetic signals, electromagnetic signals, radiologic signals.

Spinal implant system 10 includes a tracking device having an emitter array 60 that generates signals representing the position of various body reference points of the patient's anatomy. A sensor (not shown) receives signals from navigation component 40 and the emitter array 60. The sensor communicates with a processor, such as, for example, a digitizer control unit (not shown), which processes the signals from navigation component 40 and emitter array 60 to provide information regarding the trajectory of driver 26 relative to a portion of the patient's anatomy and the depth of a screw within the patient's anatomy. The processor sends this information to a monitor (not shown), which provides a visual representation of the position of driver 26 relative to the patient's anatomy to allow the medical practitioner to guide driver 26 to a desired location within the patient's anatomy.

The monitor is configured to generate an image from a data set stored in a controller, such as, for example, a computer. In some embodiments, the data set may be generated preoperatively using scanning techniques, such as, for example, a CAT scanner or MRI scanner. The image data set includes reference points for at least one body part, such as, for example, the spine of a patient, which have a fixed spatial relation to the body part. The processor is connected to the monitor, under control of the computer, and to driver 26.

The sensor receives and triangulates signals generated by navigation component 40 and an emitter array 62 to identify the relative position of each of the reference points and driver 26. The processor and the computer modify the image data set according to the identified relative position of each of the reference points during the procedure. The position and trajectory of driver 26 provided by navigation component 40 and emitter array 62 is processed by the processor and the computer and is visually displayed against the preoperative image data set stored in the computer to provide the medical practitioner with a visual representation of the trajectory of driver 26 relative to a portion of the patient's anatomy and the depth of driver 26 within the patient's anatomy.

Figure 6:
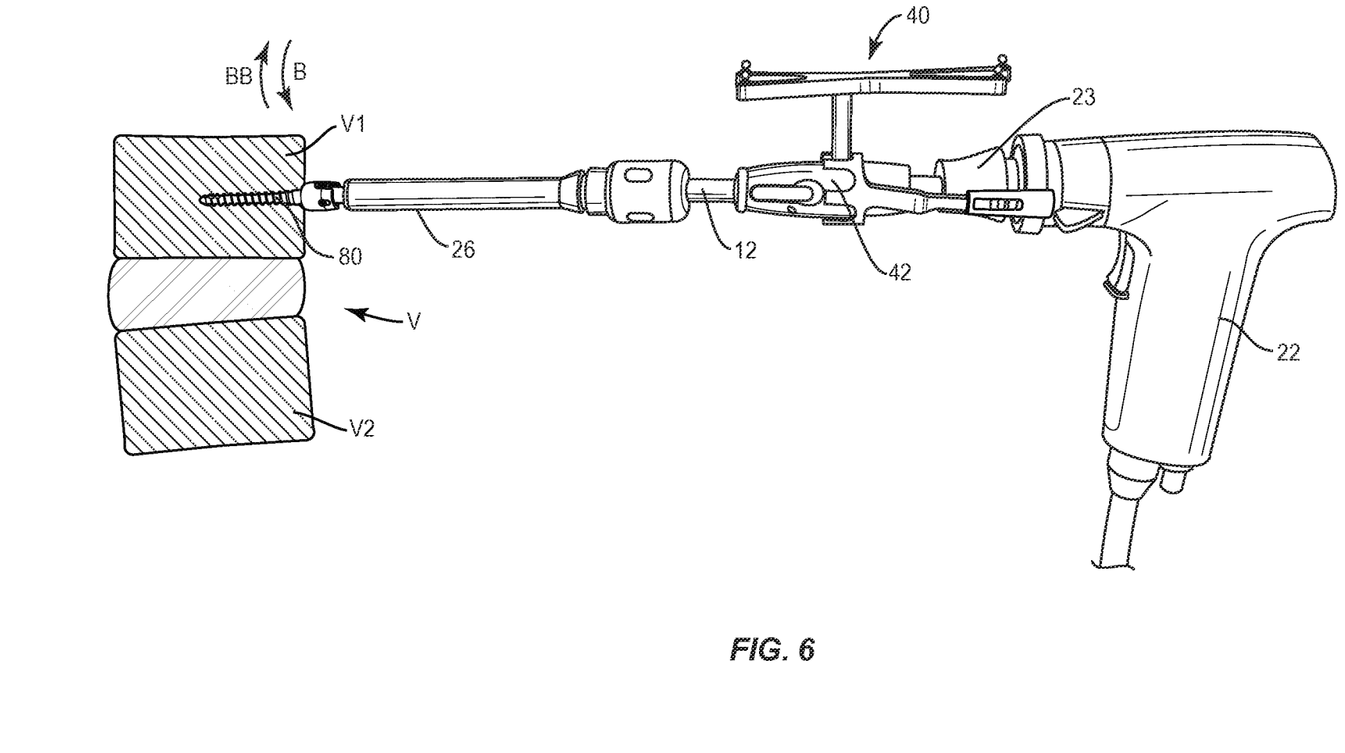
FIG. 6 is a side view of components of the system shown in FIG. 1 disposed with vertebrae.

In assembly, operation and use, spinal implant system 10 including surgical instrument adaptor 11, described herein, is employed with a surgical procedure for treatment of a spinal disorder affecting a section of a spine of a patient, as discussed herein. For example, adaptor 11 of spinal implant system 10 can be used with a surgical procedure for treatment of a condition or injury of an affected section of the spine including vertebrae V, as shown in FIG. 6. In some embodiments, one or all of the components of spinal implant system 10 can be delivered or implanted as a pre-assembled device or can be assembled in situ. Spinal implant system 10 may be completely or partially revised, removed or replaced.

For example, as shown in FIG. 6, the components of spinal implant system 10 can be employed with a surgical treatment of an applicable condition or injury of an affected section of a spinal column and adjacent areas within a body, such as, for example, vertebrae V. In some embodiments, the components of spinal implant system 10 may be employed with one or a plurality of vertebra, such as, for example, vertebra V1 and vertebra V2. To treat a selected section of the vertebrae, a medical practitioner obtains access to a surgical site including the vertebrae in any appropriate manner, such as through incision and retraction of tissues. In some embodiments, the components of spinal implant system 10 can be used in any existing surgical method or technique including open surgery, mini-open surgery, minimally invasive surgery and percutaneous surgical implantation, whereby vertebrae V are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of components of spinal implant system 10 including a surgical instrument adjacent an area within the patient's body, such as, for example, vertebra V1.

As shown in FIG. 4, shaft 12 is translated through passageway 46 of navigation component 40 such that collar 40 mates with flange 36 to lock navigation component 40 in position. As shown in FIG. 4, driver 26 is disposed with end 16 such that connection portion 24 engages cavity 30 to lock driver 26 with shaft 12. Section 28 is aligned with cavity 30 such that flange 34 engages cavity 30 for a secure fit.

As shown in FIG. 5, actuator 22 is engaged with end 14 such that portion 20 engages the mating part of actuator 22. Actuator 22 can be connected with shaft 12 either before driver 26 or after, depending on a particular surgical procedure.

Access to the surgical site is obtained and the particular surgical procedure is performed. The components of spinal implant system 10, including driver 26 and actuator 22, are employed to augment the surgical treatment. For example, a bone fastener 80 may be inserted into bone or other tissue with driver 26, for example via clockwise or counterclockwise rotation. Fastener 80 may be delivered, introduced, inserted and/or removed from the bone or other tissue of vertebrae V with driver 26. Upon completion of a surgical procedure, driver 26 may be disengaged from fastener 80, and the non-implanted components, including driver 26 may be removed from the surgical site and the incision closed.

In one embodiment, spinal implant system 10 is disassembled, as described herein, to facilitate cleaning of one or all of the components. The configuration of shaft 12 provides access to areas of driver 26, including difficult to reach areas and/or inaccessible areas due to its assembled configuration. Spinal implant system 10 may be re-assembled for use in a surgical procedure.

Spinal implant system 10 can include one or a plurality of bone fasteners such as those described herein and/or fixation elements, which may be employed with a single vertebral level or a plurality of vertebral levels. In some embodiments, the bone fasteners may be engaged with vertebrae in various orientations, such as, for example, series, parallel, offset, staggered and/or alternate vertebral levels. In some embodiments, the bone fasteners and/or fixation elements may include one or a plurality of multi-axial screws, sagittal angulation screws, pedicle screws, mono-axial screws, uni-planar screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts. In some embodiments, system 10 may comprise various instruments including the configuration of the present disclosure, such as, for example, inserters, extenders, reducers, spreaders, distractors, blades, retractors, clamps, forceps, elevators and drills, which may be alternately sized and dimensioned, and arranged as a kit, according to the requirements of a particular application.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae V. The components of spinal implant system 10 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An adaptor comprising:
   a member defining a longitudinal axis and being configured for connection to an image guide configured to generate a signal representative of a position of a surgical instrument,
   the member extending between a first end and a second end, and
   the first end including a first mating part configured for releasable engagement with a mating part of an actuator and the second end including a second mating part configured for releasable engagement with a mating part of the surgical instrument,
   wherein the member comprises a shaft that includes a circumferential flange integrally formed with the shaft, wherein the circumferential flange comprises opposite first and second end surfaces, an outer surface of the circumferential flange being continuously tapered from the second end surface to the first end surface.

2. A system comprising:
   the adaptor recited in claim 1;
   the actuator recited in claim 1; and
   the surgical instrument recited in claim 1, wherein:
   the first mating part includes a male mating part and the mating part of the actuator includes a female mating part; and
   the second mating part includes a male mating part and the mating part of the surgical instrument includes a female mating part.

3. An adaptor as recited in claim 1, wherein the second mating part is configured to prevent toggle between the member and the surgical instrument when connected with the surgical instrument.

4. An adaptor as recited in claim 1, wherein the second mating part includes a friction fit element configured to engage the mating part of the surgical instrument.

5. An adaptor as recited in claim 1, wherein the second mating part includes a resilient flange configured to engage the mating part of the surgical instrument.

6. An adaptor as recited in claim 1, wherein the second mating part includes a hexagonal cross sectional portion configured for engagement with a hex socket of the surgical instrument.

7. An adaptor as recited in claim 1, wherein the first mating part includes a square cross section configured for engagement with a square socket of the mating part of the actuator.

8. An adaptor as recited in claim 1, wherein the first mating part is configured for mating with alternate actuators.

9. An adaptor as recited in claim 1, wherein the second mating part is configured for mating with alternate surgical instruments.

10. An adaptor as recited in claim 1, wherein the member includes a bushing configured for releasable connection with the guide, the bushing being integrally formed with the shaft.

11. An adaptor as recited in claim 10, wherein the image guide includes a collar for releasable engagement with the member.

12. An adaptor as recited in claim 1, wherein the surgical instrument is a driver and is configured for load bearing.

13. A system comprising:
    the adaptor recited in claim 1; and
    the surgical instrument recited in claim 1,
    wherein the second mating part and the mating part of the surgical instrument include a keyed configuration.

14. An adaptor comprising:
    a shaft defining a longitudinal axis and including a circumferential flange being configured for connection to an emitter configured to generate a signal representative of a position of a surgical instrument,
    the shaft extending between a first end and a second end, and
    the first end including a male mating part configured for releasable engagement with a female mating part of an actuator, and the second end including a second male mating part configured for releasable engagement with a female mating part of the surgical instrument,
    wherein the shaft includes a circumferential flange integrally formed with the shaft, wherein the circumferential flange comprises opposite first and second end surfaces, an outer surface of the circumferential flange being continuously tapered from the second end surface to the first end surface.

15. An adaptor as recited in claim 14, wherein the second male mating part includes a friction fit element configured to engage the mating part of the surgical instrument.

16. An adaptor as recited in claim 14, wherein the second male mating part of the second end includes a resilient flange configured to engage the mating part of the surgical instrument.

17. A system comprising:
    the adaptor recited in claim 14; and
    the surgical instrument recited in claim 14,
    wherein the second male mating part and the mating part of the surgical instrument include a keyed configuration such that a direction of insertion of the member is controlled.

18. A surgical system comprising:
    an actuator;
    a driver;
    an image guide; and
    a member defining a longitudinal axis and being configured for connection to the image guide configured to generate a signal representative of a position of the driver, the member extending between a first end and a second end, and the first end including a first mating part configured for releasable engagement with a mating part of the actuator, and the second end including a second mating part configured for releasable engagement with a mating part of the driver, wherein the member comprises a shaft that includes a circumferential flange integrally formed with the shaft, wherein the circumferential flange comprises opposite first and second end surfaces, an outer surface of the circumferential flange being continuously tapered from the second end surface to the first end surface.

19. A surgical system as recited in claim 18, wherein:

the image guide comprises a collar defining a passageway, the collar comprising a plurality of resilient tabs that each include an inner surface that define a cutout and an opposite outer surface, the resilient tabs each including raised portion that define edges of the cutout; and the circumferential flange is configured to engage the resilient tabs to fix the shaft relative to the collar.

* * * * *

UNITED STATES PATENT AND TRADEMARK OFFICE
CERTIFICATE OF CORRECTION

PATENT NO.        : 9,451,999 B2
APPLICATION NO.   : 14/050855
DATED             : September 27, 2016
INVENTOR(S)       : Simpson et al.

Page 1 of 1

It is certified that error appears in the above-identified patent and that said Letters Patent is hereby corrected as shown below:

On the Title Page

In item (72), under "Inventors", in Column 1, Line 1, delete "Collieville," and insert -- Collierville, --, therefor.

In item (72), under "Inventors", in Column 1, Line 5, delete "McGahann," and insert -- McGahan, --, therefor.

In the Specification

In Column 6, Line 51, delete "shaft 14," and insert -- shaft 12, --, therefor.

In Column 8, Lines 24-25, delete "collar 40" and insert -- collar 42 --, therefor.

Signed and Sealed this
Twenty-seventh Day of December, 2016

Michelle K. Lee
*Director of the United States Patent and Trademark Office*